(12) United States Patent
Kong

(10) Patent No.: US 6,368,818 B1
(45) Date of Patent: Apr. 9, 2002

(54) METHODS AND COMPOSITIONS FOR THE VISUALIZATION OF CELLULAR ORGANELLES USING TETRAZOLIUM SALTS

(76) Inventor: Qingzhong Kong, 799 Dahlia St., #502, Denver, CO (US) 80220

( * ) Notice: Subject to any disclaimer, the term of this patent is extended or adjusted under 35 U.S.C. 154(b) by 0 days.

(21) Appl. No.: 09/687,342

(22) Filed: Oct. 12, 2000

Related U.S. Application Data

(62) Division of application No. 09/376,494, filed on Aug. 18, 1999, now Pat. No. 6,232,334, which is a division of application No. 09/280,094, filed on Mar. 29, 1999, now Pat. No. 6,004,989, which is a division of application No. 08/924,919, filed on Sep. 8, 1997, now Pat. No. 5,962,491, which is a division of application No. 08/715,100, filed on Sep. 17, 1996, now Pat. No. 5,703,110, which is a division of application No. 08/131,667, filed on Oct. 5, 1993, now Pat. No. 5,705,517, which is a division of application No. 08/058,739, filed on May 10, 1993, now Pat. No. 5,401,764, which is a division of application No. 07/997,703, filed on Jan. 5, 1993, now Pat. No. 5,328,919, which is a division of application No. 07/687,238, filed on Apr. 18, 1991, now Pat. No. 5,196,444.

(51) Int. Cl.$^7$ .............................. G01N 1/30; G01N 33/48

(52) U.S. Cl. .............................. 435/40.5; 435/4; 435/29

(58) Field of Search .............................. 435/40.5, 4, 29; 424/85.4

(56) References Cited

U.S. PATENT DOCUMENTS

| | | | |
|---|---|---|---|
| 5,726,009 A | 3/1998 | Connors et al. ................ | 435/4 |
| 5,736,129 A | * 4/1998 | Medenica et al. | |

OTHER PUBLICATIONS

Abe et al., 1999, *Brain Res.*, 830:146–154.
Liu et al., 1997, *J. Neurochem.*, 69(2):581–593.
Verma et al., 1997, *Nature*, 389:239–242.
Weber et al., 1999, *Histochem. J.*, 31:293–301.
Histochemical Journal vol. 31 No. 5 pp. 293–301 May 1999.*
Exp. and Toxicologic Path. vol. 51 No. 1 pp. 3–7 Jan. 1999.*
Leung et al., 1992, *Leuk. Res.*, 16(9):929–935.
Abe, K and Saito H. (1999) Both oxidative stress–dependent and independent effects of amyloid beta protein are detected by 3–(4,5–dimethylthiazol–2–yl)–2, 5–diphenyltetrazolium bromide (MTT) reduction assay. Brain Res 29;830(1):146–54.
Abe, K and Saito H. (1998) Amyloid b protein inhibits cellular MTT reduction not by suppression of mitochondrial succinate dehydrogenase but by acceleration of MTT formazan exocytosis in cultured rat cortical astrocytes. Neuroscience Res 31: 295–305.
Bakkenist, CJ, et al., (1999) Heat shock cognate 70 mutations in sporadic breast carcinoma. Cancer Res 59(17):4219–21.

Bernas, T, et al., (1999) Reduction of a tetrazolium salt, CTC, by intact HepG2 human hepatoma cells: subcellular localisation of reducing systems, Biochim Biophys Acta, 12;1451(1):73–81.
Berridge, MV, and Tan AS, (1993) Characterization of the cellular reduction of 3–(4,5–dimethylthiazol–2–yl)–2, 5–diphenyltetrazolium bromide (MTT): Subcellular localization, substrate dependence,and involvement of mitochondrial electron transport in MTT reduction 303(2): 474–482.
Brinkley, BR, et al., (1998) supernumerary centrosomes and cancer: Boveri's hypothesis resurrected. Cell Motil Cytoskeleton. 41(4):281–8, Review.
Carroll, PE, et al., (1999) Centrosome hyperamplification in human cancer: chromosome instability induced by p53 mutation and/or Mdm2 overexpression. Oncogene 18(11):1935–44.
Compton, D.A. (1999) New tools for the antimitotic toolbox. Science 286:913–914).
Cross, D., et al., (1996) Tau–like proteins associated with centrosomes in cultured cells. Exp Cell Res. 229(2):378–87.
Doxsey, S., (1998) The centrosome—a tiny organelle with big potential. Nat Genet. 20(2):104–6.
Flory, MR., et al., (2000) Identification of a human centrosomal calmodulin–binding protein that shares homology with pericentrin. Proc Natl Acad Sci U S A 23;97(1):5919–23.
Fry, AM, et al., (1998) Activity of the human centrosomal kinase, Nek2, depends on an unusual leucine zipper dimerization motif. J Bio Chem. 274(23):16304–10.
Gstaiger, M, et al., (1999) Association of human SCF(SKP2) subunit p19(SKP1) with interphase centrosomes and mitotic spindle poles. Exp Cell Res 247(2):554–62.
Hinchcliffe, EH, et al., (1999) Requirement of Cdk2–cyclin E activity for repeated centrosome reproduction in Xenopus egg extracts. Science 283(5403):851–4.
Hsu, LC and White, RL (1998) BRCA1 is associated with the centrosome during mitosis. Proc Natl Acad Sci U S A 95(22):12983–8.
Keryer,G, et al., (1999) Differential localization of protein kinase A type II isozymes in the Golgi–centrosomal area. Exp Cell Res. 249(1):131–46.

(List continued on next page.)

Primary Examiner—Jean C. Witz
Assistant Examiner—Brett Ozga
(74) *Attorney, Agent, or Firm*—Sheridan Ross P.C.

(57) ABSTRACT

The invention provides a biochemical method for visualizing cellular organelles (such as centrosome) and/or cytoskeletons (such as microtubules) through the use of crystallizing agents (such as tetrazolium salts), a kit containing crystallizing agents adapted for such uses, and to methods particularly for detecting neoplastic cells in a tissue sample, suspension, or a fluid sample by examining the cells for abnormalities of cellular organelles (such as centrosome) and/or cytoskeletons (such as microtubules) in the number and shapes.

7 Claims, 4 Drawing Sheets

(4 of 4 Drawing Sheet(s) Filed in Color)

OTHER PUBLICATIONS

Kimura, M, et al., (1999) Cell cycle–dependent expression and centrosome localization of a third human aurora/IpI1–related protein kinase, AIK3. J Biol Chem. 274(11):7334–40.

Kuo, KK, et al., (2000) Centrosome abnormalities in human carcinomas of the gallbladder and intrahepatic and extrahepatic bile ducts Hepatology 31(1):59–64.

Lingle, WL, et al., (1988) Centrosome hypertrophy in human breast tumors: implications for genomic stability and cell polarity. Proc Natl Acad Sci U S A. 95(6):2905–5.

Liu, Y, et al., (1997) Mechanism of cellular 3–(4, 5–dimethylthiazol–2–yl)–2,5–diphenyltetrazolium bromide (MTT) reduction. J Neurochem 69(2):581–93.

Mussman JG, et al., (2000) Synergistic induction of centrosome hyperamplification by loss of p53 and cyclin E overexpression. Oncogene 23;19(13):1635–46.

Passalacqua, M, et al., (1999) Protein kinase C–theta is specifically localized on centrosomes and kinetochores in mitotic cells. Biochem J 337 (Pt 1):113–8.

Pihan, GA, et al., (1998) Centrosome defects and genetic instability in malignant tumors. Cancer Res 58(17):3974–85.

Salisbury, JL, et al., (199) Microtubule nucleating capacity of centrosomes in tissue sections J Histochem Cytochem. 47(10):1265–74.

Shan, B, et al., (1999) Selective, covalent modification of beta–tubulin residue Cys–239 by T138067, an antitumor agent with in vivo efficacy against multidrug–resistant tumors. Proc Natl Acad Sci U S A 96(10):5686–5691.

Xu, X, et al., (1999) Centrosome amplification and a defective G2–M cell cycle checkpoint induce genetic instability in BRCA1 exon 11 isoform–deficient cells. Mol Cell 3(3):389–95.

Tanaka, T, et al., (1999) Centrosomal kinase AIK1 is over-expressed in invasive ductal carcinoma of the breast. Cancer Res 59(9):2041–4.

Zhou, H, et al., (1998) Tumour amplified kinase STK15/BTAK induces centrosome amplification, aneuploidy and transformation. Nat Genet. 20(2):189–93.

* cited by examiner

METHODS AND COMPOSITIONS FOR THE VISUALIZATION OF CELLULAR ORGANELLES USING TETRAZOLIUM SALTS

This application is a divisional of Ser. No. 09/376,494, filed Aug. 18, 1999, now U.S. Pat. No. 6,232,334, which is a divisional of Ser. No. 09/280,094 filed Mar. 29, 1999, now Pat. No. 6,004,989, which is a divisional of Ser. No. 08/924,919, filed Sep. 8, 1997, now U.S. Pat. No. 5,962,491, which is a divisional of Ser. No. 08/715,100, filed Sep. 17, 1996, now U.S. Pat. No. 5,703,110, which is a divisional of Ser. No. 08/131,667, filed Oct. 5, 1993, now U.S. Pat. No. 5,705,517, which is a divisional of Ser. No. 08/058,739 filed May 10, 1993, now U.S. Pat. No. 5,401,764, which is a divisional of Ser. No. 07/997,703 filed Jan. 5, 1993, now U.S. Pat. No. 5,328,919, which is a divisional of Ser. No. 07/687,238 filed Apr. 18, 1991, now U.S. Pat. No. 5,196,444.

FIELD OF THE INVENTION

The invention relates to cell biology and oncology. More specifically, this invention relates to the methods for visualizing cellular organelles (such as a centrosome) and/or cytoskeletons (such as microtubules) through the use of crystallizing agents (such as tetrazolium salts), to a kit containing crystallizing agents adapted for such use, and to methods particularly for detecting neoplastic cells in a tissue sample, suspension, or a fluid sample by examining the cells for abnormalities in the size, number and shape of cellular organelles (such as a centrosome) and/or cytoskeletons (such as microtubules).

BACKGROUND OF THE INVENTION

The characteristics and functions of cells are determined and maintained by cellular organelles and the cellular cytoskeleton. Cellular organelles include, but are not limited to, nucleus, mitochondria, peroxisomes, Golgi apparatus, lysosomes, endoplasmic reticulum, centrosome, and vacuoles. The term cytoskeleton (cytoskeletal structures) refers to an extensive scaffolding of fibrillar elements, including the three filamentous systems: microfilaments (or actin filaments), microtubules, and intermediate filaments. It may also include linin filaments. The components of the cytoskeleton are involved in diverse cellular functions ranging from mitosis to cell motility to signal transduction. Among these organelles and cytoskeletal structures, centrosome, microtubules, mitochondrion, endoplasmic reticulum, lysosomes, and nuclear envelope are most important.

The centrosome, a central body (or the major microtubule-organizing center (MTOC) of the cell) plays a key role in the temporal and spatial distribution of the interphasic and mitotic microtubule network. Therefore, the centrosome could be considered a major determinant of the overall organization of the cytoplasm and of the fidelity of cell division (Hsu, L. C. and White, R. L. (1998) *Proc Natl Acad Sci U S A* 27;95(22):12983–8). Cytoplasmic organization, cell polarity and the equal partition of chromosomes into daughter cells at the time of cell division, once and only once in each cell cycle, are all ensured through the actions of tightly regulated centrosomal function (Tanaka, T., et al., (1999) *Cancer Res* 59(9): 2041–4). Centrosome association occurs throughout the mammalian cell cycle, including all stages of mitosis, and determines the number, polarity, and organization of interphase and mitotic microtubules (Tanaka, T., et al., (1999) *Cancer Res* 59(9): 2041–4; Pihan, G. A., et al., (1998) *Cancer Res* 58(17):3974–85). The main function of the centrosome is the nucleation of microtubules, and the controlled cycle of its duplication, the two duplicated entities functioning as mitotic spindle poles during subsequent cell division. Centrosomes and their associated microtubules direct events during mitosis and control the organization of animal cell structures and movement during interphase. Although the precise mechanisms by which duplicated chromosomes are equally segregated during mitosis are largely unknown, the centrosome is believed to play an important role(s) in the formation of bipolar spindles (Tanaka, T., et al., (1999) *Cancer Res* 58(17):3974–85). The microtubule nucleating ability of centrosomes of tissue sections is retained even after several years of storage as frozen tissue blocks (Salisbury, J. L., et al., (1999) *J. Histochem. Cytochem.* 47(10):1265–74).

In animal cells, the centrosome is composed of two centrioles surrounded by the so-called pericentriolar material (PCM), which consists of a complex thin filament network and two sets of appendages.

Malignant tumors generally display abnormal centrosome profiles, characterized by an increase in size and number of centrosomes, by their irregular distribution, abnormal structure, aberrant protein phosphorylation, and by increased microtubule nucleating capacity in comparison to centrosomes of normal tissues (Lingle, W. L. et al., (1998) *Proc Natl Acad Sci U S A* 95(6): 2950–5; Xu, X., et al., (1999) *Mol Cell* 3(3):389–95; Brinkley, B. R., et al., (1998) *Cell Motil Cytoskeleton* 41(4):281–8; Doxsey, S. (1998) *Nat Genet* 20(2):104–6; Kuo, K. K., et al., (2000) *Hepatology* 31(1):59–64). Among the abnormalities, centrosome hyperamplification is found to be more frequent in a variety of tumor types (Carroll, P. E., et al., (1999) *Oncogene* 18;18 (11):1935–44; Hinchcliffe, E. H., et al., (1999) *Science* 283(5403):851–4; Xu, X., et al., (1999) *Mol Cell* 3(3):389–95).

Centrosome consists of many key proteins such as, SKP1p, cyclin-dependent kinase 2-cyclin E (Cdk2-E) (Hinchcliffe, E. H., et al., (1999) *Science* 283(5403): 851–4), kendrin (Flory, M. R., et al., (2000) *Proc Natl Acad Sci U S A* 23;97(11):5919–23), Protein kinase C-theta (Passalacqua, M., et al., (1999) *Biochem J* 337(Pt 1): 113–8), EB1 protein. Recently, a variety of cell cycle-regulated kinases or tumor suppressor genes are located in or are core components of the centrosome. They include Nek2 (Fry, A. M., et al., (1999) *J Biol Chem* 274(23): 1304–10), protein kinase A type II isozymes (Keryer, G., et al., (1999) *Exp Cell Res* 249(1):131–146), heat shock Cognate 70 (HSC70) (Bakkenist, C. J., et al., (1999) *Cancer Res* 59(17):4219–21), PH33 (Nakadai, T., et al., (1999) *J Cell Sci* 112 (Pt9):1353–64), AIKs (Kimura, M., et al., (1999) *J Biol Chem* 274(11)7334–40), human SCF(SKP2) subunit p19 (SKP1) (Gstaiger, M., et al., (1999) *Exp Cell Res* 247(2) 554–62), STK15/BTAK (Zhou, H., et al., (1998) *Nat Genet* 20(2): 189–93), C-Nap1 (Fry, A. M., et al., (1998) *J Cell Biol* 274(23): 1304–10), Tau-like proteins (Cross, D., et al., (1996) *Exp Cell Res* 229(2):378–87), cyclin E (Carroll, P. E., et al., (1999; Mussman, J. G., et al., (2000) *Oncogene* 23;19(13):1635–46), p53, retinoblastoma protein pRB and BRCA1(Hsu, L. C., et al., (1998) *Proc Natl Acad Sci U S A* 95(22):12983–8). These proteins are required in the initiation of DNA replication and mitotic progression (Gstaiger, M., et al., (1999) *Exp Cell Res* 15;247(2):554–62).

Microtubules, a filamentous system, are linear polymers of alpha- and beta (the beta1, beta2, and beta4 isotypes)-tubulin heterodimers. Except for being a frame of cellular membrane and organelles, microtubules may play an important role in other aspects. Microtubules are involved in diverse cellular functions ranging from mitosis to cell motility to signal transduction. Microtubules are the major constituents of mitotic spindles, which are essential for the separation of chromosomes during mitosis (Shan, B., et al., (1999) *Proc Natl Acad Sci U S A* 96(10):5686–5691). They are nucleated by centrosome through the kinetochores of the centrosome. The spindle is a microtubule-based superstructure that assembles during mitosis to separate replicated DNA. Chromosome attachment to and movement on the spindle is intimately tied to the dynamics of microtubule polymerization and depolymerization. The sister chromatid pairs must maintain a stable attachment to spindle microtubules as the microtubules interconvert between growing and shrinking states. Drugs that are currently used in cancer therapy were designed to perturb microtubule shortening (depolymerization) or lengthening (polymerization) (Compton, D. A., et al., (1999) *Science* 286:913–914).

Other cytoskeletons such as membrane skeleton, microvilli, cilia, flagella, microfilaments, actin filaments, contractile ring, and intermediate filaments are all important in the organization of the cytoplasm and of the fidelity of cell division.

In addition to the centrosome and microtubules, other cellular organelles or cellular sub organelles such as mitochondrion, chromosomes, chromatin, nuclei, nuclear matrix, nuclear lamina, core filaments, nuclear envelope (NEs), nuclear pore complexes (NPCs), nuclear membrane, centrioles, pericentriolar material (PCM), mitotic spindle, spindle pole bodies (SPBs), contractile rings, proteasomes, telomere, plasma membranes, Golgi complexes, Golgi apparatus, endoplasmic reticulum (ER), endosomes, peroxisomes, proteasomes, phagosomes, ribosomes, are all important in maintaining a cell's life. Endoplasmic reticulum, e.g. is the site of synthesis and maturation of proteins.

Therefore, identification of a novel less-costing, simple, and effective method for the visualization of cellular organelles and/or cytoskeleton is indeed necessary in cell biology, cell cycle, signal transduction, development biology, and cancer research.

However, most available methods for the visualization of the centrosome and other important cellular organelles and/or cytoskeleton are based on the antigen-antibody reaction (Lingle, W. L. et al., (1998) *Proc Natl Acad Sci U S A* 95(6): 2950–5; Xu, X., et al., (1999) *Mol Cell* 3(3):389–95; Brinkley, B. R., et al., (1998) *Cell Motil Cytoskeleton* 41(4):281–8; Doxsey, S. (1998) *Nat Genet* 20(2):104–6; Carroll, P. E., et al., (1999) *Oncogene* 18;18(11):1935–44; Hinchcliffe, E. H., et al., (1999) *Science* 283(5403):851–4; Xu, X., et al., (1999) *Mol Cell* 3(3):389–95). These techniques have been proved to be very costly, poorly reproducible, time consuming, and requiring of very strict conditions. Particularly, these methods can not be used to demonstrate the dynamic states of cells.

It is against this background, this invention provides a biochemical method for visualizing cellular organelles and/or cytoskeletons, by treating tissues or cells with crystallizing agents. The crystallizing agents or compounds used in this invention are a variety of tetrazolium salts. The cell-mediated reduction of some tetrazolium salts has long been used as a cell number-counting method (Berridge, M V, and Tan, A S., (1993) *Arch Biochem Biophys* 303(2): 474–482; Bernas, T., et al., (1999) *Biochim Biophys Acta* 12;1451(1):73–81; Abe, K., and Saito, H., (1999) *Brain Res* 29;830(1):146–54; Liu, Y., et al., (1997). *J Neurochem* 69(2):581–93; Abe, K., and Saito, H., (1998) *Neuroscience Res* 31: 295–305). In the visualization of cellular organelles and/or cytoskeletons, the application of tetrazolium salts has never been mentioned. The inventor of this invention has found that tetrazolium salts can specifically concentrate on cellular organelles and/or cytoskeletons of a variety of cells and tissues, with the formation of visible crystals in these places. The visualization of cellular organelles and/or cytoskeletons using a biochemical approach instead of the complicated immune methods provides a less costly, very simple, quick, and effective method for the visualization of cellular organelles and/or cytoskeleton. It provides a tool with great potential in studying cell biology, structural biology, cell cycle, signal transduction, development biology, and oncology.

SUMMARY OF THE INVENTION

The inventor has found that enzymes, such as dehydrogenases, are highly expressed in various tissues, and cell lines, particularly in cancerous cells. Except for mitochondrion, this enzyme is widely expressed in other structures of the cells such as, but not limited to, centrosomes, microtubules, endoplasmic reticulum, flagella, nuclear envelopes, lysosomes and other structures as mentioned above. When crystallizing agents, such as tetrazolium salts, are present, cellular enzymes, mainly succinate dehydrogenase (SDH), which is usually anchored on the cellular structures, will reduce the tetrazolium salts into related crystals that can be visualized under proper conditions. Additionally, the formation of crystals may act as a restraint to the separation of the duplicable organelles and to the movement of cytoskeletons.

Based on this discovery, the present invention features a method for visualizing cellular organelles and/or cytoskeletons, in tissue or in cell suspension, by treating tissue or cells with one or more crystallizing agents. The method includes obtaining a tissue sample or a fluid sample containing multiple cells from a variety of sources such as, but not limited to mammalian, microorganisms, and cancers; then fixing the tissue sample or cultured cell sample; contacting the tissue sample or cell sample with a crystallizing agent under conditions that permit the formation of visible crystals through the reduction of said crystallizing agent by the enzymes located in said cellular organelles and/or cytoskeletons in said cells or tissues; and then visualizing cellular organelles and/or cytoskeletons having crystals formed on them. The method allows for easy and quick visualization of cellular organelles and/or cytoskeletons that are usually observed through complex immunofluorescence staining or under electronic microscope.

Due to the high expression of the dehydrogenases in cancer cells, this invention is particularly useful in detecting the changes of the number and shapes of the neoplasm in their cellular organelles and/or cytoskeletons, thereby detecting neoplastic disease in the tissue or differentiating neoplastic cells from normal cells.

Since the dehydrogenating reaction usually takes place in the viable cells, this invention is particularly useful in monitoring the changes of the number and shapes of the cellular organelles and/or cytoskeletons of the cells at different time points. Therefore, this invention is helpful for better understanding of the regulating mechanisms in cell cycle and signal transduction, particularly for screening the drugs that specifically target cellular organelles and/or cytoskeletons of the cells for their actions.

The enzymes of this invention can be any protein(s) present in cytoskeletons and/or cellular organelles such as membrane skeleton, microvilli, cilia, flagella, microfilaments, actin filaments, contractile ring, microtubules and intermediate filaments or proteins present in cell organelles or cellular sub organelles such as centrosome, centrioles, pericentriolar material (PCM), mitotic spindle, spindle pole bodies (SPBs), mitochondrion, chromosomes, chromatin, nuclei, nuclear matrix, nuclear lamina, core filaments, nuclear envelope (NEs), nuclear pore complexes (NPCs), nuclear membrane, contractile rings, lysosomes, telomere, plasma membranes, Golgi complexes, Golgi apparatus, endoplasmic reticulum (ER), endosomes, peroxisomes, proteasomes, phagosomes, ribosomes. The enzyme of this invention can be a component of these organelles and/or cytoskeletons or be stored in these organelles and/or cytoskeletons. The enzymes of this invention can be a dehydrogenase such as alcohol dehydrogenase, beta-hydroxysteroid dehydrogenase, inosine monophosphate dehydrogenase, glucose alpha.-dehydrogenase, glucose-6-phosphate dehydrogenase, glyceraldehyde-3-phosphate dehydrogenase, glycerol-3 phosphate dehydrogenase (mGPDH), glyceraldehyde 3-phosphate dehydrogenase, malate dehydrogenase, 3-.alpha.-hydroxysteroid dehydrogenase, lactate dehydrogenase, L-glutamate dehydrogenase, leucine dehydrogenase, aldehyde dehydrogenase, sarcosine dehydrogenase, amine dehydrogenase, telomerase, choline dehydrogenase, fructose dehydrogenase, succinate dehydrogenase, and sorbitol dehydrogenase. The enzyme can also be other proteins such as, but not limited to, pericentrin, cp140, centrin, .gamma.-tubulin, .alpha.-tubulin, .beta.-tubulin (U.S. Pat. No. 5,972, 626), SKP1p, cyclin-dependent kinase 2-cyclin E (Cdk2-E), Protein kinase C-theta, EB1 protein, Nek2, protein kinase A type II isozymes, heat shock Cognate 70 (HSC70), PH33, AIKs, human SCF(SKP2) subunit p19(SKP1), STK15/BTAK, C-Nap1, Tau-like proteins, p53, retinoblastoma protein pRB and BRCA1. The enzyme of this invention may be other oxidation reductases. The enzyme of present invention is most likely to be succinate dehydrogenase.

The crystallizing agents of this invention may be any compounds that can be reduced by cellular enzymes located in the organelles or cytoskeletons, with the formation of visible crystals. It is preferably of tetrazolium compounds. Tetrazolium compounds refer to the compounds that contain tetrazole, tetrazolyl, tetrazolo-, or tetrazyl, and tetrazotic acids. Tetrazolium compounds may also be tetrazotized compounds. Example of crystallizing agents is pABT (p-Anisyl Blue Tetrazolium Chloride); pApNBT, p-Anisyl-p-Nitro Blue Tetrazolium Chloride; BSPT, Thiazolyl blue (2-2'-Benzothiazolyl-5-styryl-3-(4'-phthalhydrazidyl) tetrazolium chloride); BT, Blue tetrazolium chloride; BTSPT, 2-(2'-Benzothiazolyl)-5-styryl-3-(4'-phthalhydrazidyl)-tetrazolium chloride; CTC, (5-Cyano-2,3-ditolyl tetrazolium chloride); DMDPT, [3-4,5-Dimethylthiazol-2-yl)-2,5-diphenyl]tetrazolium Bromide, 1-[4,5-dimethylthiazol-2-yl]-2,5-diphenyltetrazolium bromide; DSNBT, Distyryl nitroblue tetrazolium chloride; (1H)-tetrazole; IDNTT, Iodonitrotetrazoilum chloride; INT, Iodo Nitro Tetrazolium Violet Chloride, p-iodo nitrotetrazolium violet (2-(4-iodophenyl)-3-(4-nitrophenyl)-5-phenyltetrazolium chloride; INpT, 2-(p-iodophenyl)-p-nitrophenyl-5-phenyltetrazolium chloride; mNBT, m-Nitro Blue Tetrazolium Chloride; mNNT, m-Nitro Neotetrazolium Chloride; MNSTC, 2,2-bis(2-methoxyl-4-nitro-5-sulfophenyl)-2H-tetrazolium-5-carboxanilide; MTS: 3-(4,5-dimethylthiazol-2-yl)-5-(3-carboxymethoxyphenyl)-2-(4-sulfophenyl)-2H-tetrazolium salt; MTT, tetrazolium bromide, thiazolyl blue tetrazolium bromide, (3→4,5-dimethylthiazol-2-yl!-2,5-diphenyltetrazolium bromide); NBMT, Nitro Blue Monotetrazolium Chloride; NBT, p-Nitro Blue Tetrazolium Chloride, Nitro blue tetrazolium chloride (2,2'-di-nitrophenyl-5,5'-diphenyl-3,3'-(3,3'-dimethoxy-4,4'-diphenylene)ditetrazolium chloride); NT, Neotetrazolium chloride (2,2',5,5'-Tetraphenyl-3,3'(p-diphenylene)-ditetrazolium chloride; NTV, Nitrotetrazolium Violet; Thiazolyl blue; TB, tetrazolium blue chloride (3,3'→3,3'-dimethoxy(1,1'-biphenyl)-4,4'-diyl]-bis(2,5-diphenyl-2H-tetrazolium)dichloride); NBT, Nitroblue tetrazolium chloride; oTTR, o-Tolyl Tetrazolium Red; PCTMB, sodium 3'-[1-[(phenylamino)-carbonyl]-3,4-tetrazolium]-bis(4-methoxy-6-nitro)benzene-sulfonic acid hydrate; PNBT, p-Nitro Blue Tetrazolium Chloride; PTB, Piperonyl Tetrazolium Blue; pTTR, p-Tolyl Tetrazolium Red; TC-NBT, Thiocarbamyl nitro blue tetrazolium chloride (2,2'-di-p-nitrophenyl-5,5'-di-p-thiocarbamylphenyl-3,3'[3, 3'-dimethoxy-4,4'-biphenylene]-ditetrazolium chloride; TNBT, Tetranitroblue tetrazolium chloride; TPTT, 1,3,5-triphenyltetrazolium; TR, TTC, TPT, Tetrazolium Red (2,3, 5-triphenyltetrazolium chloride); TV, Tetrazolium violet, Violet Tetrazolium, 2,3,5-Triphenyl-2-H-tetrazolium chloride, 2,5-diphenyl-3-[.alpha.-naphthyl]-tetrazolium chloride, 2,5-diphenyl-3-[1-naphthyl]-2H-tetrazolium chloride; VTB, Veratryl tetrazolium blue; WST-1, 4-[3-(4-iodophenyl)-2-(4-nitrophenyl)-2H-5-tetrazolio]-1,3-benzene disulfonate; XTT, 2,2-bis(2-methoxyl-4-notro-5-sulfophenyl)-2H-tetrazolium-5-carboxanilide.

The crystallizing agents of this invention are materials that can be reduced by cellular enzymes located in the organelles or cytoskeletons, with the formation of visible crystals. Among the agents tested, tetrazolium salts are most effective. Cellular enzymes, mainly SDH, which is usually anchored on the cellular structures, will reduce the tetrazolium salts into related crystals that can be visualized under proper conditions. The visible crystals are formed where the said enzymes are located, therefore providing a method for viewing the enzyme-hosting cellular structures or components. In addition, the inventor has also found that tetrazolium compounds have differential targeting structures. For example, TV forms crystals in centrosome, therefore specifically crystallizing centrosomes; MTT forms crystals in microtubules, mitochondrion, and nuclear envelopes or endoplasmic reticulum; and TR forms crystals in envelopes and/or other structures close to envelopes such as endoplasmic reticulum. Therefore different tetrazolium salts or analogues may specifically crystallize certain cellular organelles or sub-organelles. It also suggested that SDH may have different forms or be located widespread in cells.

The tissue sample or cell sample can be from any source, such as, but not limited to mammalian, microorganism, vegetable, or parasite. The tissue sample or cell sample of this invention may be normal or neoplastic, from any part of a mammalian e.g., brain, neck, breast, lung, esophagus, liver, stomach, kidney, colon, rectum, skin, connective tissue, lymph node, blood vessel, nerve, ovary, bladder, uterus, testis, and bone. The tissue sample can be fresh, e.g., a biopsy sample, or can be from an archived sample, e.g., a frozen sample or a sample embedded in paraffin. The cell sample can from fluid, tissue cavity, tissue homogenate, tissue lavage, biopsy, cell lines, bone marrow and blood. The cell sample can be fresh, e.g., blood or bone marrow sample, or can be from an archived sample, e.g., a frozen cell lines.

Cellular organelles and cytoskeletons can have difference appearances, depending on sample origins, concentration of the agents used, and the duration of the contacting time.

Samples can be processed using methods known in the art, which includes tissue isolation and dissociation to release individual cells. Cells can be spun onto coverslips ("cytospun"), fixed, and subjected to visualization under microscope. Cells are preferably visualized directly under microscope in culturing flasks.

Any crystallizing agent that can be reduced by cellular enzymes with the formation of visible crystals can be used in the invention. It includes any tetrazolium compound, not limited to those described above such as TR, MTT, and TV. Any new compounds that contain tetrazolium tetrazole, tetrazolyl, tetrazolo-, or tetrazyl will fall in the scope of this invention. New tetrazolium compounds further include tetrazotic acids and tetrazotized compounds.

Crystals formed by the reduction of said crystallizing agents can be detected using detection methods known in the art, e.g., microscope. Naked eyes can also tell the occurrence of the reaction by examining the change of the color in the culture medium. The method of the invention for visualizing cellular structures may be used with other techniques such as immunofluorescence, immunoperoxidase staining, flow cytometry, or Western blot hybridization.

The present invention is also directed to a kit containing one or more crystallizing agents, such as tetrazolium red, MTT, and tetrazolium violet. The kit may comprise a pharmaceutically acceptable carrier medium.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentality, combinations, and methods particularly pointed out in the appended claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWINGS

The file of this patent contains at least one drawing in color. Copies of this patent with color drawings will be provided by the Patent and Trademark Office upon request and payment of the necessary fee.

The accompanying drawings, which are incorporated in and form a part of the specification, illustrate the preferred embodiments of the present invention, and together with the descriptions serve to explain the principles of the invention.

DETAILED DESCRIPTION OF THE PREFERRED EMBODIMENTS

Figure 1:
FIG. 1 shows the crystallization of centrosomes of 9L gliosarcoma tumor cells following treatment with TV.

The work leading to this invention has shown that enzymes such as dehydrogenases are extensively expressed in many cellular organelles and cytoskeletons. Dehydrogenases are significantly high in various malignant tumors of different human histogenetic types.

The present invention provides a simple, less costly, rapid, and effective method for viewing cellular organelles and cytoskeletons, particularly for the visualization of the cellular organelles and cytoskeletons, of various cancer cells, in a tissue sample or cell sample from a mammalian patient. The method is based on the discovery of a positive correlation between the expression of dehydrogenases and the presence of organelles and cytoskeletons. The changes of cellular organelles and cytoskeletons (such as the centrosome and microtubules) in the shape or numbers in cells or tissues are reflected by the change of the dehydrogenases in these structures. Normal cells express less of these enzymes. Taking the centrosome as an example, if it contains one or more of the defects, a cell is considered to have centrosomal abnormalities, and thus to indicate a cancerous state. Such centrosome defects include, but not limited to, hypertrophic centrosomes, or supernumerary centrosomes. A tissue sample is typically scored as neoplastic if a substantial fraction of its cells display centrosomal abnormalities. By viewing the number and shape of the centrosome or microtubules, the cell cycle status of the cell examined may also be determined.

The method of this invention involves obtaining a tissue sample or single cells from a variety of sources, preferably of a mammalian. The primarily prepared tissue or cells are fixed or cultured before being contacted with one or more crystallizing agents under conditions that permit formation of visible crystals through the reduction of said crystallizing agent by the enzymes located in said cellular organelles and/or cytoskeletons in said cells or tissues. Once the crystals are formed, the targeted cellular organelles and/or cytoskeletons can be visualized under a microscope. By comparing the changes in the number and shapes of said cellular organelles and/or cytoskeletons, cancerous cells may be distinguished from the related normal ones.

The crystallizing agents are compounds or compositions that are the substrates of cellular enzymes. For practicing the present invention, a crystallizing agent that can be converted into visible crystals by the enzymes located in cellular structures is necessary. A crystallizing agent suitable for use in the present invention can be obtained commercially or can be synthesized. Preferably, the crystallizing agent is one or more tetrazolium salts such as but not limited to, tetrazolium violet, tetrazolium blue, MTT or tetrazolium red, and the enzyme is a dehydrogenase such as succinate dehydrogenase. Crystallizing agents such as tetrazolium blue, tetrazolium violet and tetrazolium red are catalyzed by the enzyme, such as SDH, with the formation of crystals. The crystals formed in cellular organelles can be visualized under a microscope. In another aspect, the present invention provides a kit containing one or more crystallizing agents suitable for visualizing cellular organelles and cytoskeletons.

Unless defined otherwise, all technical and scientific terms used herein have the same meaning as commonly understood by one of ordinary skill in the art to which this invention pertains. Although any methods and materials similar or equivalent to those described herein can be used in the practice of the present invention, the preferred methods and materials are described.

As used herein, the term "crystallizing agent" refers to a substance that, when present in a living cell or medium containing enzymes that catalyze dehydrogenating reactions, can form crystals. Preferred crystallizing agents are tetrazolium salts and related derivatives or analogues. Examples of crystallizing agent include substrates of succinate dehydrogenase. Examples of substrates of succinate dehydrogenase are pABT (p-Anisyl Blue Tetrazolium Chloride); pApNBT, p-Anisyl-p-Nitro Blue Tetrazolium Chloride; BSPT, Thiazolyl blue (2-2'-Benzothiazolyl-5-styryl-3-(4'-phthalhydrazidyl) tetrazolium chloride); BT, Blue tetrazolium chloride; BTSPT, 2-(2'-Benzothiazolyl)-5-styryl-3-(4'-phthalhydrazidyl)-tetrazolium chloride; CTC, (5-Cyano-2,3-ditolyl tetrazolium chloride); DMDPT, [3-(4, 5-Dimethylthiazol-2-yl)-2,5-diphenyl]tetrazolium Bromide, 1-[4,5-dimethylthiazol-2-yl]-2,5-diphenyltetrazolium bromide; DSNBT, Distyryl nitroblue tetrazolium chloride; (1H)-tetrazole; IDNTT, Iodonitrotetrazoilum chloride; INT, Iodo Nitro Tetrazolium Violet Chloride, p-iodo nitrotetrazolium violet (2-(4-iodophenyl)-3-(4-nitrophenyl)-5-phenyltetrazolium chloride; INpT, 2-(p-iodophenyl)-p-nitrophenyl-5-phenyltetrazolium chloride; mNBT, m-Nitro Blue Tetrazolium Chloride; mNNT, m-Nitro Neotetrazolium Chloride; MNSTC, 2,2-bis(2-methoxyl-4-nitro-5-sulfophenyl)-2H-tetrazolium-5-carboxanilide; MTS: 3-(4,5-dimethylthiazol-2-yl)-5-(3-carboxymethoxyphenyl)-2-(4-sulfophenyl)-2H-tetrazolium salt; MTT, tetrazolium bromide, thiazolyl blue tetrazolium bromide, (3→4,5-dimethylthiazol-2-yl!-2,5-diphenyltetrazolium bromide); NBMT, Nitro Blue Monotetrazolium Chloride; NBT, p-Nitro Blue Tetrazolium Chloride, Nitro blue tetrazolium chloride (2,2'-di-nitrophenyl-5,5'-diphenyl-3,3'-(3,3'-dimethoxy-4,4'-diphenylene)ditetrazolium chloride); NT, Neotetrazolium chloride (2,2',5,5'-Tetraphenyl-3,3'(p-diphenylene)-ditetrazolium chloride; NTV, Nitrotetrazolium Violet; Thiazolyl blue; TB, tetrazolium blue chloride (3,3'→3,3'-dimethoxy(1,1'-biphenyl)-4,4'-diyl]-bis(2,5-diphenyl-2H-tetrazolium)dichloride); NBT, Nitroblue tetrazolium chloride; oTTR, o-Tolyl Tetrazolium Red; PCTMB, sodium 3'-[1-[(phenylamino)-carbonyl]-3,4-tetrazolium]-bis(4-methoxy-6-nitro)benzene-sulfonic acid hydrate; PNBT, p-Nitro Blue Tetrazolium Chloride; PTB, Piperonyl Tetrazolium Blue; pTTR, p-Tolyl Tetrazolium Red; TC-NBT, Thiocarbamyl nitro blue tetrazolium chloride (2,2'-di-p-nitrophenyl-5,5'-di-p-thiocarbamylphenyl-3,3'[3, 3'-dimethoxy-4,4'-biphenylene]-ditetrazolium chloride; TNBT, Tetranitroblue tetrazolium chloride; TPTT, 1,3,5-triphenyltetrazolium; TR, TTC, TPT, Tetrazolium Red (2,3, 5-triphenyltetrazolium chloride); TV, Tetrazolium violet, Violet Tetrazolium, 2,3,5-Triphenyl-2-H-tetrazolium chloride, 2,5-diphenyl-3-[.alpha.-naphthyl]-tetrazolium chloride, 2,5-diphenyl-3-[1-naphthyl]-2H-tetrazolium chloride; VTB, Veratryl tetrazolium blue; WST-1, 4-[3-(4-iodophenyl)-2-(4-nitrophenyl)-2H-5-tetrazolio]-1,3-benzene disulfonate; XTT, 2,2-bis(2-methoxyl-4-notro-5-sulfophenyl)-2H-tetrazolium-5-carboxanilide. Preferably, the crystallizing agent is selected from one or more member of the group consisting of tetrazolium salts including tetrazolium violet, MTT, tetrazolium red, and tetrazolium blue. Most preferably, one or more tetrazolium salts are used when the catalyzing enzyme, such as SDH, is up regulated (e.g. cancerous cells).

As used herein, the term "enzyme" refers to a substance that, when present in a living cell or medium containing their substrates, catalyses dehydrogenating reactions. Enzymes can function in several ways: by dehydrogenating substances such as succinic acid or succinate (hereinafter referred to as "substrate") to provide cellular energy, or by converting salts such as tetrazolium salts into related formazan crystals. The enzymes that may catalyze the formation of crystals are, but not limited to, alcohol dehydrogenase, beta-hydroxysteroid dehydrogenase, inosine monophosphate dehydrogenase, glucose alpha.-dehydrogenase, glucose-6-phosphate dehydrogenase, glyceraldehyde-3-phosphate dehydrogenase, glycerol-3 phosphate dehydrogenase (mGPDH), malate dehydrogenase, 3-.alpha.-hydroxysteroid dehydrogenase, lactate dehydrogenase, L-glutamate dehydrogenase, leucine dehydrogenase, aldehyde dehydrogenase, sarcosine dehydrogenase, amine dehydrogenase, succinate dehydrogenase, choline dehydrogenase, fructose dehydrogenase, oxidation reductases and sorbitol dehydrogenase. Preferably, the enzyme is one of the group consisting of inosine monophosphate dehydrogenase, telomerase, glucose-6-phosphate dehydrogenase, malate dehydrogenase, lactate dehydrogenase, and succinate dehydrogenase. Most preferably, the enzyme is SDH.

As used herein, the term "cytoskeleton" refers to a complex network of protein filaments traversing the cell cytoplasm. It is not simply a passive feature of the cell that provides structural integrity, it is a dynamic structure that is responsible for whole-cell movement, changes in cell shape, and contraction; it provides the machinery to move organelles from one place to another in the cytoplasm. Some cytoskeletal fibers may connect to organelles or provide tracks along which organelles and/or small molecules move. It is recently evidenced that the cytoskeleton is a master organizer of the cell's cytoplasm, furnishing binding sites for the specific localization of ribonucleic acids (RNAs) and proteins that were once thought to diffuse freely through the cytoplasm. The cytoskeleton is also responsible for signal transmission. Activities of the cytoskeleton depend mainly on just three principal types of protein assemblies: actin filaments, microtubules, and intermediate filaments. Each type of filament or microtubule is formed from the specific association of protein monomers. The dynamic aspects of the cytoskeletal structures arise from accessory proteins that control the length of the assemblies, their position within the cell, and the specific-binding sites along the filaments and microtubules for association with protein complexes, organelles, and the cell membrane. Thus, present invention also includes the crystallization of these proteins, protein monomers, and protein filaments. Dynamically, crystallization of microtubules, centrosomes, and other cytoskeletons may interfere with the message (or signal) transmission or cell motility, and consequently make the cells lacking of mitosis motive force. The crystallization of nuclear envelopes may block the duplication of chromatins, and therefore obstruct the formation of sister cells.

As used herein, the term "organelle" refers to a subcellular unit or a subcellular structure defined by membrane. The organelle in this invention includes, but is not limited to, nucleus (containing most of the cellular DNA and being the site of synthesis of cellular RNAs), nuclear matrix, nuclear lamina, core filaments, nuclear envelope (NEs), nuclear pore complexes (NPCs), and nuclear membranes. The organelle of the present invention also include mitochondrion (generating the most cellular ATP through oxidation of small molecules), endoplasmic reticulum (ER, a network of membranes in which glycoproteins and lipids are synthesized), Golgi complexes or Golgi apparatus (directing membrane constituents to appropriate places), lysosomes (degrading proteins, nucleic acids and lipids), and vacuoles (large fluid-filled organelles that store many nutrient and waste molecules, and also participate in the degradation of cellular proteins and other micromolecules). The organelle in this invention further include chromosomes, nucleosome, chromatin, centromere, centrosome, centrioles, pericentriolar material (PCM), mitotic spindle, spindle pole bodies (SPBs), contractile rings, kinetochore, lysosomes, telomere, plasma membranes, endosomes, peroxisomes (metabolizing hydrogen peroxide), proteasomes, phagosomes, and ribosomes. Each type of organelle plays a unique role in the growth, metabolism, and metastasis of the tumor cells, and each contains a collection of specific proteins or enzymes that catalyze requisite chemical reactions. Some of this specificity resides in the organelle membranes, to which a number of the enzymes and other proteins are bound. Dehydrogenases, particularly succinate dehydrogenase, are found to be highly expressed in such organelles of a variety of cancer cells. Through SDH catalyzed dehydrogenating reaction, some chemicals such as tetrazolium salts can be reduced to the related formazan crystals. The crystallization of the organelles and/or cytoskeleton that have high level of SDH will have their functions and structures destroyed. The proteins or enzymes that are located in the structures that are rich in SDH will be inactivated or frozen. Therefore, the methods of this invention and agents used in the methods can be used for screening anti-cancer agents.

As used herein, the term "effective dose" refers to the amount of the agents that result in a clear visualization of the targeted cellular structures. Suitable doses of the agent can be determined using well-known methods, or can be chosen after trying an escalating dose.

As used herein, the term "neoplasm, tumor or cancer" refers to any neoplastic disorder, including carcinomas, sarcomas and carcino-sarcomas. Specific types of neoplastic disorders include, without limitation, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullary carcinoma, mastocytoma, mesotheliorma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonal carcinoma, squamous cell carcinoma, base cell carcinoma, fibrosarcoma, myxoma, myxosarcoma, liposarcorna, chondrosarcoma, osteogenic sarcoma, leukemia, and the metastatic lesions secondary to these primary tumors. In general, any neoplastic lesion, including granulomas, may be included according the present invention. Therefore, the "cancer cells" in this invention also includes the cancer-supporting components such as tumor endothelial cells.

A basis of the present invention is the unexpected finding that substances such as tetrazolium salts exhibit potent cellular structure-crystallizing activity. While the mechanism of action is not fully understood, and not wishing to be bound by any particular theory, it is believed that these agents exert their cell structure crystallizing effect through formation of crystals on the key cellular structures including organelles and/or cytoskeleton. The formation of a variety of crystals can make the targeted structures such as centrosomes, microtubules, mitochondrion and nuclear envelope visible under a microscope. The crystallization of the centrosome will deactivate many key enzymes located on it. The crystallization of microtubules not only ceases mitosis but also causes mechanic injury of the targeted cells. The crystallization of microtubules and nuclear envelopes further interfere with the mobility of the cell and the transmission of cellular messages. Therefore this method may be very useful in screening anticancer agents, in cell biology study such as cell cycle, structural biology and signal transduction. Because the intracellular concentration of endogenous enzymes such as succinate dehydrogenases in the cancer cells is higher than that in normal cells, this method may be useful for differentiating cancer cells.

In one aspect of the invention one or more crystallizing agents are used to visualize cellular organelles or cytoskeletons. While it is possible to use one crystallizing agent, it is believed to be preferable to use more crystallizing agents. The combination of more than one agent is preferable for visualizing cells, and most preferable for differentiating cancer cells from the normal ones. Preferably, the crystallizing agent is a substrate of the enzymes. In a particularly preferred embodiment, the substrates of the enzymes are the substrates of succinate dehydrogenase. Examples of the substrates of succinate dehydrogenase are tetrazolium salts and their analogues or derivatives. Tetrazolium salts are compounds with tetrazole, tetrazolyl, or tetrazolo- structure. Example of tetrazolium salts is, not limited to, MTT, TB, Tetrazolium Blue, HTT, tetrazolium red, TPF, ITT, INT, tetrazolium violet (TV), INPT, neotetrazolium chloride, NBT, diformazan of NBT, TNBT, TC-NBT, TTD, MTS, WST-1, XTT, DDTT, and PCTT. The combination of the crystallizing agents is also determined by the targets that are to be detected. For example, tetrazolium violet (TV) forms crystals mainly in the centrosome, and therefore, it can be used to specifically visualize centrosomes, while MTT forms crystals in microtubules, mitochondrion, and nuclear envelopes; and TR forms crystals in envelopes and/or other structures close to envelopes such as endoplasmic reticula. Therefore different tetrazolium salts or analogues may specifically crystallize certain cellular organelles or sub-organelles.

According to a method of this invention, an effective amount of a crystallizing agent is administered to a cell sample or tissue sample, preferably a cell sample, to visualize cellular organelles and/or cytoskeletons of cells. The required dosage will depend on the nature of the cell, contacting period of time, cell number, thickness of tissue section, crystallizing agents that will be used, and the visualizing targets. In general, a suitable effective dose of the crystallizing agent will be in the range of about 0.1 to about 1000 microgram (ug) per milliliter (ml), preferably in the range of about 1.0 to about 100 ug per milliliter. The dose is preferably administered directly into the medium containing cells or tissue sample.

In another aspect of the invention one or more crystallizing agents are used in a kit to visualize cellular organelles and cytoskeletons. While it is possible to use the crystallizing agent(s) alone, it is believed preferable to present it as part of a formulation. Such formulations are preferably for visualizing cells, and most preferably for differentiating cancer cells from the normal ones. In accordance with this aspect of the invention, the kits comprise at least one crystallizing agent in an effective dose together with one or more carriers and optionally other ingredients. Preferred carriers include inert, non-toxic liquids (e.g., culture media, buffered saline, water, culturing medium). If desired, the kit may also contain minor amounts of nontoxic auxiliary substances such as wetting or emulsifying agents, pH buffering agents, and the like. Compositions comprising such carriers and adjuvants may be formulated, and the resulting formulations may be sterilized, using well-known conventional methods and techniques. Methods for administration are also well known in the art.

The invention is further described by the following examples which are illustrative of specific modes of practicing the invention and are not intended as limiting the scope of the invention as defined by the appended claims.

The terms and abbreviations used in the instant examples have their normal meanings unless otherwise designated. For example "$\mu$l" refers to microliter or microliters; "$\mu$g" refers to microgram or micrograms; "mg" refers to milligram or milligrams; "mil" means milliliter or milliliters. Unless specified otherwise, commercially available chemicals were used without purification. All scientific and technical terms have the meanings as understood by one with ordinary skill in the art. The specific example which follow illustrates the in vitro effect of certain representative compositions and are not to be construed as limiting the invention in sphere or scope. The procedures and materials may be adapted to variation in order to produce compositions and methods embraced by this invention but not specifically disclosed. Further variations of the methods to produce the same compositions in somewhat different fashion will be evident to one skilled in the art.

The present invention is more specifically illustrated by the following Examples. However, it should be understood that the present invention is not limited to such Examples, but various changes and modifications can be made without departing from the scope and spirit of the invention.

EXAMPLES

Example 1

Preparation of Cells From Fresh Tissues for Cellular Organelle Visualization

Cells suspensions were removed from surgical resection specimens of intracranially or subcutaneously established gliosarcomas in rats by removing samples (0.5–1.0 cm square) of tissue and then mincing the samples with a razor blade in PBS at room temperature. Minced tissue was then washed in PBS and resuspended in 2 ml aliquot of PBS containing 2.0 U/ml of collagenase and 0.2 U/ml DNase, and then incubated for 2 hours at room temperature. During the incubation, the samples were rotated end over end. Following collagenase and DNase digestion, the samples were strained on a 100 micrometer nylon filter (Nytex, Small Parts, Inc., Miami Lakes, Fla.), pelleted, washed in PBS, by sequential centrifugation at 325 G. Then they were transferred into a flask for culture as described in Examples 3–6 (below). Cells can also be obtained from fresh tissue, peripheral blood, bone marrow, and lymph nodes and treated in a similar manner.

Example 2

Visualization of Centrosomes of SHP77 (SCLC) Cells Following Treatment With TV 9L gliosarcoma tumor cells (4000) obtained by the method described in example 1 were seeded in 48 well plate one day before being exposed to tetrazolium violet (TV, a substrate of SDH) at the concentration of 50 $\mu$g/ml. The Modified DMEM media was used in this example. As shown in FIG. 1, centrosomes, usually one in each cell (J, #1–6), were crystallized at the poles, with the cell viability being significantly reduced (see data in Example 1).

After being treated under the same condition, the centro some of CNS1 tumor cells were all crystallized (not shown).

Example 3

Figure 2:
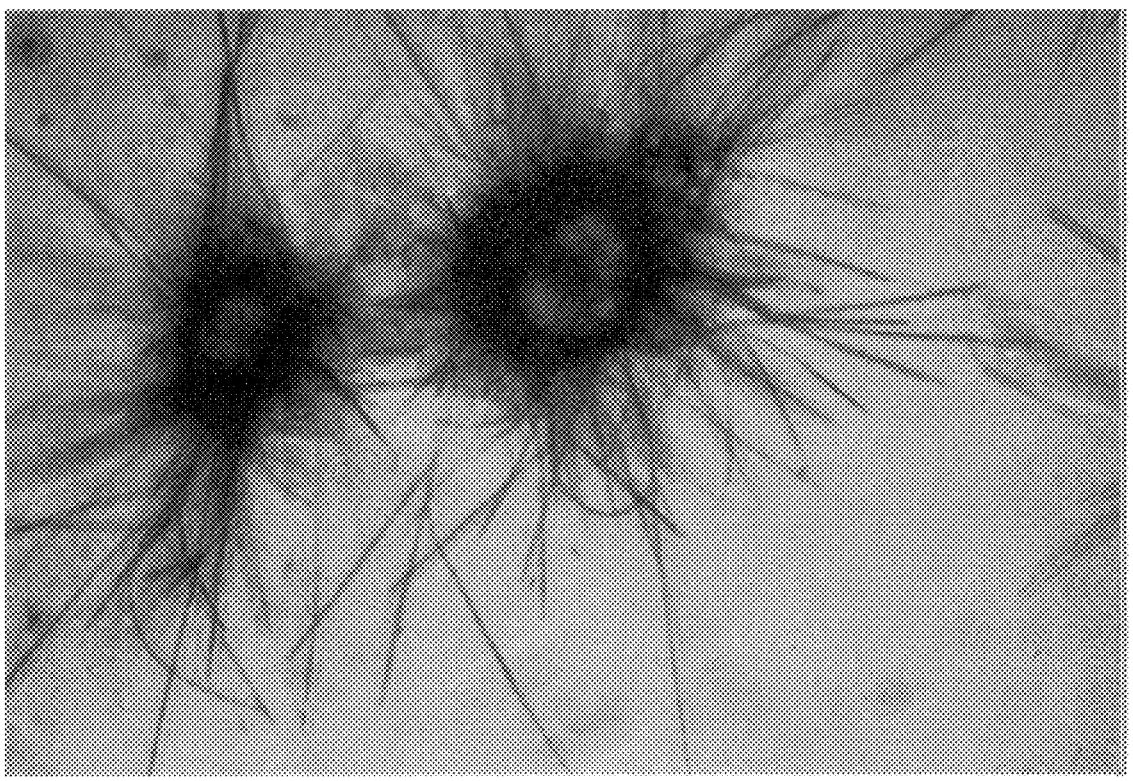
FIG. 2 shows the crystallization of microtubules of 9L gliosarcoma cancer cells following treatment with MTT.

Visualization of Microtubules of 9L Gliosarcoma Cancer Cells Following Treatment With MTT 9L cancer cells were exposed to MTT (50 ug/ml) at the same condition as described in Example 2. The tumor cells (4000) were seeded one day before being treated with MTT. As can be seen in FIG. 2, the microtubules and nuclear envelopes were frozen by the crystals formed on them.

Example 4

Figure 3:
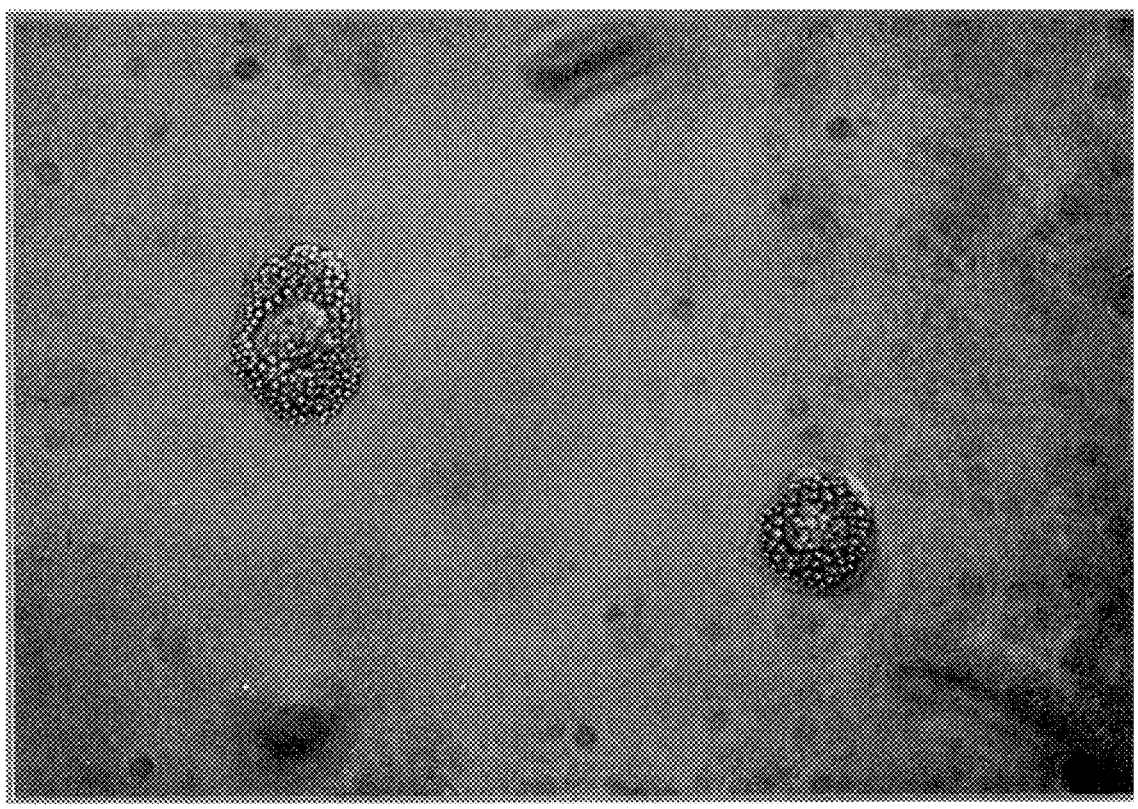
FIG. 3 shows the crystallization of mitochondrion or lysosomes of 9L gliosarcoma cells following treatment with MTT.

Crystallization of Mitochondrion or Lysosomes of 9L Gliosarcoma Cells Following Treatment With MTT 9L gliosarcoma cancer cells were exposed to MTT (50 ug/ml)—a substrate of SDH. The tumor cells (4000) were seeded one day before being treated with MTT. As can be seen in FIG. 3, the mitochondrion were crystallized by the crystals formed on them.

Example 5

Figure 4:
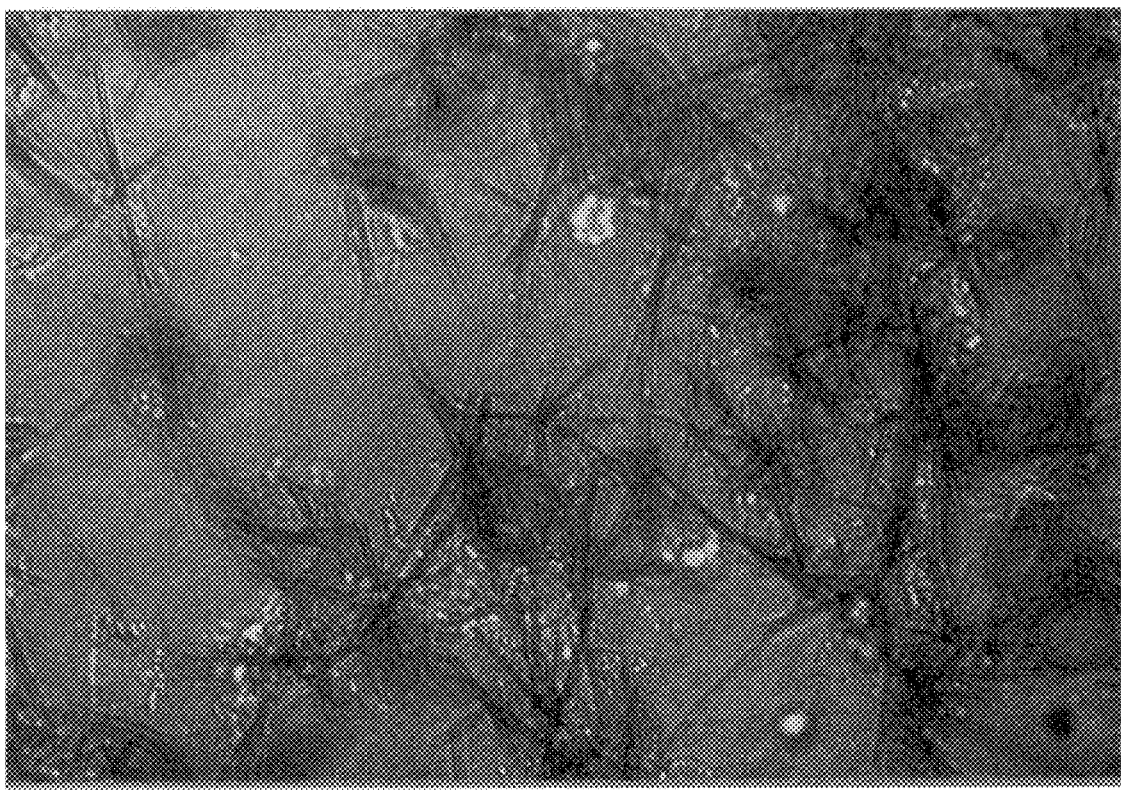
FIG. 4 shows the crystallization of nuclear envelopes of endoplasmic reticulum of 9L gliosarcoma cells following treatment with TR.

Crystallization of Nuclear Envelopes and/or Endoplasmic Reticulum of 9L Gliosarcoma Cells Following Treatment With TR 9L gliosarcoma cancer cells were exposed to TR (50 ug/ml)—a substrate of SDH. The tumor cells (4000) were seeded one day before being treated with TR. As can be seen in FIG. 4, nuclear envelopes in most cells were crystallized.

These kinds of crystal on the cellular structures (described above in Examples 2 through 5) could be inhibited by heating cells in hot water (>60° C.) for more than 30 minutes, or by prior incubation with SDH inhibitor (nitropropionic acid, a typical irreversible SDH inhibitor).

Although the mechanisms are still to be explored, and not wishing to be bound by any particular theory, the inventor believes that the formation of crystals may be used to visualize the cellular structures such as cell membrane, plasma membrane, organelles, and cytoskeletons.

As the formation of crystals is based on the dehydrogenating reaction, and the dehydrogenating enzymes are usually highly expressed in cancer cells, this method therefore has relatively high specificity. When used for visualizing cancer cells, crystallizing agent(s) will target tumor cells more selectively, leaving the normal cells crystallized less. Therefore, the formation of crystals on the cancerous cell can be used in diagnostic methods.

The foregoing description is considered as illustrative only of the principles of the invention. Since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A method for visualizing the structure of cellular organelles and/or cytoskeletons selected from the group consisting of centrosomes and microtubules, in tissue or in cell suspension, said method comprising the steps of:

(a) obtaining a tissue sample or cell sample, said sample containing a plurality of cells, wherein said tissue sample or cell is selected from the group consisting of normal mammalian tissue or cell, pathologic mammalian tissue or cell, and neoplastic tissue or cell;

(b) contacting said tissue sample or cell sample with one or more crystallizing agents under conditions that permit formation of visible crystals through the reduction of said crystallizing agent by the enzymes in said cellular organelles and/or cytoskeletons selected from the group consisting of centrosomes and microtubules of said cells or tissues; and (c) visualizing said crystals formed in said cellular organelles and/or cytoskeletons selected from the group consisting of centrosomes and microtubules.

2. The method according to claim 1, wherein the crystallizing agent is selected from the group consisting of tetrazolium salts, tetrazolium analogues and related derivatives containing tetrazolium.

3. The method according to claim 1, wherein the crystallizing agent is selected from the group consisting of p-Anisyl Blue Tetrazolium Chloride, p-Anisyl-p-Nitro Blue Tetrazolium Chloride, Thiazolyl blue (2-2'-Benzothiazolyl-5-styryl-3-(4'-phthalhydrazidyl)tetrazolium chloride), Blue tetrazolium chloride, 2-(2'-Benzothiazolyl)-5-styryl-3-(4'-phthalhydrazidyl)-tetrazolium chloride, 5-Cyano-2,3-ditolyl tetrazolium chloride), [3-(4,5-Dimethylthiazol-2-yl)-2,5-diphenyl]tetrazolium Bromide, 1-[4,5-dimethylthiazol-2-yl]-2,5-diphenyltetrazolium bromide, Distyryl nitroblue tetrazolium chloride, (1H)-tetrazole, Iodonitrotetrazoilum chloride, Iodo Nitro Tetrazolium Violet Chloride, p-iodo nitrotetrazolium violet, (2-(4-iodophenyl)-3-(4-nitrophenyl)-5-phenyltetrazolium chloride, 2-(p-iodophenyl)-p-nitrophenyl-5-phenyltetrazolium chloride, m-Nitro Blue Tetrazolium Chloride, m-Nitro Neotetrazolium Chloride, 2,2-bis(2- methoxyl-4-nitro-5-sulfophenyl)-2H-tetrazolium-5-carboxanilide, 3-(4,5-dimethylthiazol-2-yl)-5-(3-carboxymethoxyphenyl)-2-(4-sulfophenyl)-2H-tetrazolium salt, tetrazolium bromide, thiazolyl blue tetrazolium bromide, 3→4,5-dimethylthiazol-2-yl!-2,5-diphenyltetrazolium bromide, Nitro Blue Monotetrazolium Chloride, p-Nitro Blue Tetrazolium Chloride, Nitro blue tetrazolium chloride, 2,2'-di-nitrophenyl-5,5'-diphenyl-3,3'-(3,3'-dimethoxy-4,4'-diphenylene)ditetrazolium chloride, Neotetrazolium chloride, 2,2',5,5'-Tetraphenyl-3,3'(p-diphenylene)-ditetrazolium chloride, Nitrotetrazolium Violet; Thiazolyl blue, tetrazolium blue chloride, 3,3'→3,3'-dimethoxy(1,1'-biphenyl)-4,4'-diyl]-bis(2,5-diphenyl-2H-tetraz olium)dichloride, Nitroblue tetrazolium chloride, o-Tolyl Tetrazolium Red, sodium 3'-[1-[(phenylamino)-carbonyl]-3,4-tetrazolium]-bis(4methoxy-6-nitro)benzene-sulfonic acid hydrate, p-Nitro Blue Tetrazolium Chloride, Piperonyl Tetrazolium Blue, p-Tolyl Tetrazolium Red, Thiocarbamyl nitro blue tetrazolium chloride, 2,2'-di-p-nitrophenyl-5,5'-di-p-thiocarbamylphenyl-3,3'[3,3'-dimethoxy-4,4'-biphenylene]-ditetrazolium chloride, Tetranitroblue tetrazolium chloride, 1,3,5-triphenyltetrazolium, Tetrazolium Red, 2,3,5-triphenyltetrazolium chloride), Tetrazolium violet, Violet Tetrazolium, 2,3,5-Triphenyl-2-H-tetrazolium chloride, 2,5-diphenyl-3-[.alpha.-naphthyl]-tetrazolium chloride, 2,5-diphenyl-3-[1-naphthyl]-2H-tetrazolium chloride, Veratryl tetrazolium blue, 4-[3-(4-iodophenyl)-2-(4-nitrophenyl)-2H-5-tetrazolio]-1,3-benzene disulfonate, and 2,2-bis(2-methoxyl-4-notro-5-sulfophenyl)-2H-tetrazolium-5-carboxanilide.

4. The method according to claim 1, wherein the concentration of crystallizing agents is in the range of between about 0.1 µg/ml to about 1.0 mg/ml.

5. The method of claim 1, wherein said neoplastic tissue or cell is selected from the group consisting of carcinoma, sarcoma, carcinosarcoma, leukemia, or lymphoma.

6. The method according to claim 1, wherein said neoplastic tissue or cell is selected from the group consisting of acute lymphocytic leukemia, acute myelocytic leukemia, acoustic neuroma, adenocarcinoma, angiosarcoma, astrocytoma, basal cell carcinoma, bile duct carcinoma, bladder carcinoma, bone originated tumor, bone sarcoma, brain tumor, breast cancer, bronchogenic carcinoma, carcinoma, cervical cancer, chondrosarcoma, chordoma, choriocarcinoma, chronic lymphocytic leukemia, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, glioma, heavy chain disease, hemangioblastoma, hepatic carcinoma, hodgkin's lymphoma, leiomyosarcoma, leukemia, liposarcoma, lung carcinoma, lymphangioendotheliosarcoma, lymphangiosarcoma, medullary carcinoma, medulloblastoma, melanoma, meningioma, mesothelioma, multiple myeloma, myxosarcoma, neuroblastoma, non-Hodgkin's lymphoma, pancreatic cancer, oligodendroglioma, osteogenic sarcoma, ovarian cancer, pancreatic carcinoma, papillary carcinoma, papillary adenocarcinoma, pinealoma, polycythemia vera, acute promyelocytic leukemia, prostate cancer, rectal cancer, renal cell carcinoma, retinoblastoma, rhabdomyosarcoma, sarcoma, sebaceous gland carcinoma, seminoma, small cell lung carcinoma, squamous cell carcinoma, stomach carcinoma, synovioma, sweat gland carcinoma, testicular tumor, uterus carcinoma, Waldenstrom's macroglobulinemia, Wilms'tumor, and the endothelial cells thereof.

7. The method according to claim 1, wherein said crystallizing agents are tetrazolium violet for visualization of centrosomes and MTT for visualization of microtubules.

* * * * *

UNITED STATES PATENT AND TRADEMARK OFFICE
CERTIFICATE OF CORRECTION

PATENT NO. : 6,368,818 B1
APPLICATION NO. : 09/687342
DATED : April 9, 2002
INVENTOR(S) : Qingzhong Kong Page 1 of 1

It is certified that error appears in the above-identified patent and that said Letters Patent is hereby corrected as shown below:

On the cover page of patent, Related U.S. Application Data, field (62), the text should be cancelled:

"Division of application No. 09/376,494, filed on Aug. 18, 1999, now Pat. No. 6,232,334, which is a division of application No. 09/280,094, filed on Mar. 29, 1999, now Pat. No. 6,004,989, which is a division of application No. 08/924,919, filed on Sep. 8, 1997, now Pat. No. 5,962,491, which is a division of application No. 08/715,100, filed on Sep. 17, 1996, now Pat. No. 5,703,110, which is a division of application No. 08/131,667, filed on Oct. 5, 1993, now Pat. No. 5,705,517, which is a division of application No. 08/058,739, filed on May 10, 1993, now Pat. No. 5,401,764, which is a division of application No. 07/997,703, filed on Jan. 5, 1993, now Pat. No. 5,328,919, which is a division of application No. 07/687,238, filed on Apr. 18, 1991, now Pat. No. 5,196,444."

Column 1, lines 16-19 the text should be cancelled:

"This application is a divisional of Ser. No. 09/376,494, filed Aug. 18, 1999, now U.S. Pat. No. 6,232,334, which is a divisional of Ser. No. 09/280,094 filed Mar. 29, 1999, now Pat. No. 6,004,989, which is a divisional of Ser. No. 08/924,919, filed Sep. 8, 1997, now U.S. Pat. No. 5,962,491, which is a divisional of Ser. No. 08/715,100, filed Sep. 17, 1996, now U.S. Pat. No. 5,703,110, which is a divisional of Ser. No. 08/131,667 which is a divisional of Ser. No. 08/058,739 filed May 10, 1993, now U.S. Pat. No. 5,401,764, which is a divisional of Ser. No. 07,997,703 filed Jan. 5, 1993, now U.S. Pat. No. 5,328,919, which is a divisional of Ser. No. 07/687,238 filed Apr. 18, 1991, now U.S. Pat. No. 5,196,444."

Signed and Sealed this

Twenty-eighth Day of April, 2009

JOHN DOLL
*Acting Director of the United States Patent and Trademark Office*